United States Patent [19]

Bossart et al.

[11] Patent Number: 4,533,520
[45] Date of Patent: Aug. 6, 1985

[54] CIRCUIT FOR CONSTANT TEMPERATURE OPERATION OF A CATALYTIC COMBUSTIBLE GAS DETECTOR

[75] Inventors: Clayton J. Bossart, Monroeville; Thomas C. Fatur, Delmont, both of Pa.

[73] Assignee: Mine Safety Appliances Company, Pittsburgh, Pa.

[21] Appl. No.: 627,302

[22] Filed: Jul. 2, 1984

[51] Int. Cl.³ .................................... G01N 27/16
[52] U.S. Cl. ................... 422/96; 73/27 R; 324/DIG. 1; 422/98
[58] Field of Search .............. 422/96, 95, 94, 97, 422/98; 73/27 R, 23; 324/DIG. 1, 464; 323/367

[56] References Cited

U.S. PATENT DOCUMENTS 3,429,178 2/1967 Durbin .................. 73/27 R
3,932,807 1/1976 Wilson .................... 73/23

FOREIGN PATENT DOCUMENTS 2075195 11/1981 United Kingdom ........... 73/23
234739 1/1969 U.S.S.R. ..................... 422/98

Primary Examiner—Arnold Turk
Assistant Examiner—Carol M. Delahunty
Attorney, Agent, or Firm—Thomas H. Murray

[57] ABSTRACT

A catalytic gas detector circuit in which a resistive gas detector element is common to two bridge circuits, and wherein the resistance and temperature of the detector element are maintained essentially constant. This permits the use of a dynamic compensator element without encountering hysteresis effects and improves the response time of the circuit.

7 Claims, 3 Drawing Figures

CIRCUIT FOR CONSTANT TEMPERATURE OPERATION OF A CATALYTIC COMBUSTIBLE GAS DETECTOR

BACKGROUND OF THE INVENTION

In the past, combustible gas detector circuits have been devised comprising a bridge circuit containing, as one of its four impedances, a heated combustible gas detector. Such detector circuits are described, for example, in U.S. Pat. No. 4,317,796 and British Pat. No. 2,091,882. The resistive gas detector, whose resistance is temperature dependent, comprises a catalyst that promotes combustion of combustible gases, thereby providing additional heat to the detector. A variety of such detectors are known and used including, for example, a coil of platinum wire whose surface has been activated to combust hydrocarbons or the bead-type detector described in U.S. Pat. No. 3,092,799, suitably comprising a platinum wire coil embedded in a bead incorporating a combustion catalyst. The resistance of a detector of this type will change in response to changes in sample gas humidity and thermal conductivity. While it is possible to provide a dynamic compensator element in series with the detector in one leg of the bridge to provide correction for changes in sample gas humidity and thermal conductivity, most circuits of this type encounter hysteresis problems. That is, the presence of two dynamic elements in one leg of the bridge circuit (i.e., the compensator and detector) induces opposite and confusing signals to the circuit element resulting in hysteresis effects. For this reason, most constant temperature sensors substitute a fixed resistor for the compensator element, thus sacrificing correction for humidity and thermal conductivity changes. Most prior art catalytic combustible gas detectors of this type utilize conventional Wheatstone bridge circuits which are normally powered at either constant voltage or constant current. In either case, response time is relatively slow.

SUMMARY OF THE INVENTION

In accordance with the present invention, a new and improved catalytic combustible gas detector is provided which overcomes the disadvantages of prior art circuits described above. Specifically, the invention provides a dual-bridge circuit wherein the detector element is common to both bridges and operates at a constant temperature. In this way, a change in combustible gas concentration does not produce the thermal delay normally associated with constant voltage or constant current operation. As a consequence, response time is significantly decreased.

In prior art circuits, catastrophic failure or damage to the detector element and deteriorated performance is possible if the sensor is subjected to extremely high levels of combustible gas due to thermal run-away. In the present invention, constant temperature operation automatically prevents thermal run-away of the detector element.

Using conventional operating modes, the catalytic combustion sensor response to a given concentration of a specific combustible gas normally can be made to "plateau" (i.e., remain reasonably constant over a range of operating temperatures of the detector element). The width of this range is a function of the specific catalyst system and in some cases can be quite narrow. A change in ambient temperature can then change the detector element operating temperature to the point where the sensitivity response to the circuit changes due to a change in catalyst activity. In contrast, the invention described herein enables constant response over a wide range of ambient temperatures.

Some catalyst systems using conventional operation lose a portion of their activity and, therefore, sensor response with continuous exposure to combustible gas levels in the LEL (lower explosion limit) range. The constant temperature operation of the present invention obviates this problem by forcing the catalyst system to constant activity.

While catalytic combustion detectors are normally used to monitor the total level of combustible gases, the constant temperature operating mode of the present invention provides a selectivity for certain applications. In the case of a mine fire, for example, it is often desirable to monitor the concentrations of individual gases behind a fire seal to indicate the trend of the fire. It is especially important to monitor for hydrogen to insure that water sealing fire-fighting techniques are not generating hydrogen by contact with a hot coal seam. Since methane is virtually certain to be present also, a conventional combustible gas sensor will offer no discrimination for hydrogen since combustion of hydrogen increases the catalyst temperature to the point where methane also burns even with the sensor bridge operated at low current or voltage. Operation at a relatively low constant temperature, however, provides preferential combustion of hydrogen in the presence of methane which has a much higher ignition temperature on a palladium catalyst.

Structurally, the catalytic gas detector of the invention comprises first and second bridge circuits each having input terminals and output terminals and a common impedance connected between the terminals of the respective bridge circuits, this common impedance comprising a resistive gas detector element. Means are provided for deriving a signal indicative of gas concentration from across the output terminals of the first bridge circuit. A control element such as a transistor varies the voltage across the bridge circuits, the transistor being controlled in response to an unbalance in the second bridge circuit to maintain the effective resistance of the resistive gas detector element essentially constant.

The above and other objects and features of the invention will become apparent from the following detailed description taken in connection with the accompanying drawings which form a part of this specification, and in which.

Figure 1:
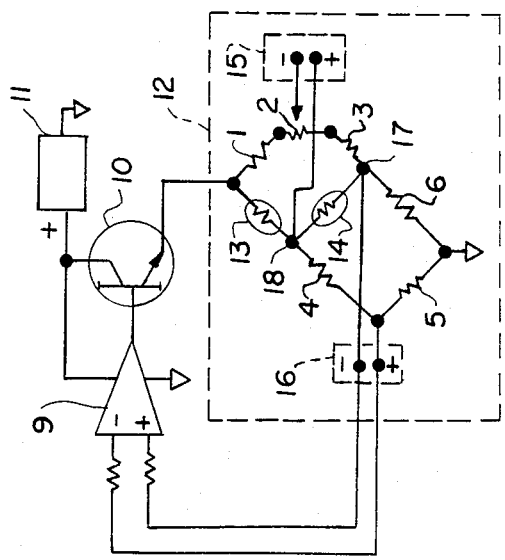
FIG. 1 is a schematic circuit diagram of one embodiment of the invention.

With reference now to the drawings, and particularly to FIG. 1, a power supply 11 is connected to a dual-Wheatstone bridge circuit 12 through control transistor 10. The upper bridge consists of a compensator element 13, a detector element 14, fixed bridge leg resistors 1 and 3, and a zeroing potentiometer 2. The detector element 14, for example, may comprise a platinum wire covered by a conventional coating containing palladium, which produces increased temperature in the presence of an explosive gas. The compensator element 13 is also preferably formed from platinum wire; however its coating is non-catalytic and, therefore, does not produce increased temperature in response to an explosive gas. The compensator element 13, however, does compensate for changes in sample gas humidity and thermal conductivity of the detector element 14. The signal output from the upper bridge circuit appears at terminals 15 and is normally further amplified and conditioned to provide a readout in terms of percent gas or percent LEL. (i.e., Lower Explosion Limit at which a combustible gas, in the presence of oxygen, will ignite).

The second or lower bridge consists of the same detector element 14 in the upper bridge and fixed leg resistors 4, 5 and 6. If desired, one or more of these fixed leg resistors may be replaced by variable resistors in order to provide greater flexibility, allowing the operating temperature of detector 14 to be adjusted as desired. From the foregoing, it will be apparent that an input terminal 17 of the first bridge circuit is common with an output terminal 17 of the second bridge circuit, that an input terminal 18 of the second bridge circuit is common with an output terminal 18 of the first bridge circuit, and that the detector 14 is connected between the common terminals.

The output appearing at terminals 16 of the second bridge circuit is maintained at null by the combined action of operational amplifier 9 and transistor 10. That is, any unbalance at output terminals 16 is amplified to bias transistor 10 and change the voltage at the junction of resistor 1 and compensator 13 to bring the lower bridge back into null balance at output terminal 16. Since bridge legs 4, 5 and 6 are fixed resistors, the null balance action forces detector 14 to maintain a constant resistance, which necessarily means constant temperature.

If it is assumed, for example, that detector element 14 is in a combustible gas environment, its temperature will tend to rise, thereby unbalancing the lower bridge circuit. This causes the operational amplifier 9 to change the bias on transistor 10, thereby lowering the voltage at the junction of elements 13 and 1. Because of this drop in voltage, the temperature and resistance of compensator element 13 drop to their original state, thereby unbalancing the upper bridge circuit such that an output appears at terminals 15 indicative of the explosive gas concentration. The unbalance signal occurs because the compensator element 13 is forced to a lower resistance with the decrease in applied voltage. Of course, if the explosive gas atmosphere is no longer present, the temperature and resistance of detector element 14 will tend to fall such that amplifier 9 and transistor 10 raise the voltage at the junction of elements 1 and 13, thereby bringing the upper bridge back into balance.

Figure 2:
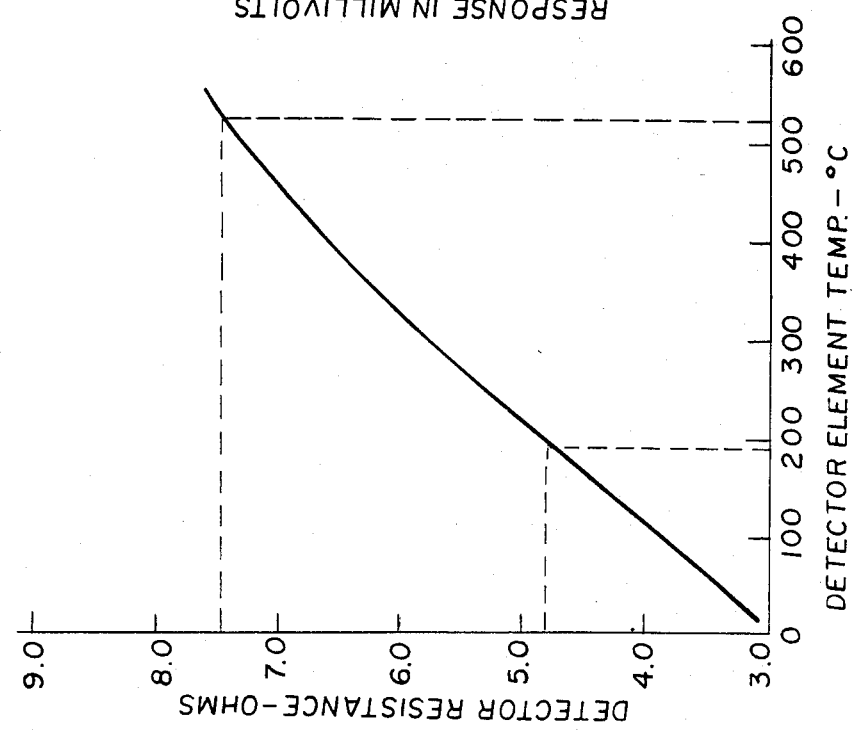
FIG. 2 is a plot of detector resistance versus detector element temperature for a typical gas detecting element of the invention.

In a typical embodiment of the invention, the power supply 11 can comprise an 8-voltage AC-to-DC supply; while resistors 1, 3, 4 and 5 are each 1000 ohms. Elements 13 and 14 are compensator and detector bead elements, respectively, each having the resistance-temperature characteristic shown in FIG. 2. Empirical tests using a constant current bridge circuit under optimum conditions, show that the resistance of a typical detector 14 at 50% LEL methane is 7.5 ohms. Consequently, by fixing resistor 6 at this value, detector 14 was also fixed at 7.5 ohms and, therefore, at 525° C. as shown by FIG. 2.

Figure 3:
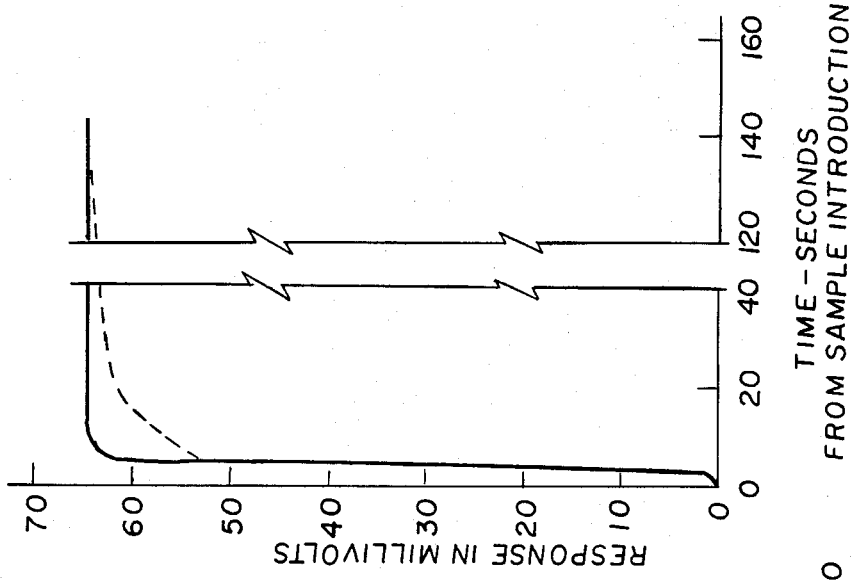
FIG. 3 is a plot of time versus voltage showing the constant temperature response time with the present invention as contrasted with the response time under constant current conditions.

In FIG. 3, the broken line illustrates the constant current response to 50% LEL methane (2.5% methane). The solid line shows the response under the same conditions but with constant temperature operation of the detector element. Note that the response characteristics are essentially identical under either condition; however the response time is dramatically improved with constant temperature operation.

Although the invention has been shown in connection with a certain specific embodiment, it will be readily apparent to those skilled in the art that various changes in form and arrangement of parts may be made to suit requirements without departing from the spirit and scope of the invention.

We claim as our invention:

1. A catalytic gas detector circuit comprising:
   first and second bridge circuits, each having input and output terminals wherein an input terminal and an output terminal of said first bridge circuit are common with an output terminal and an input terminal of said second bridge circuit, respectively;
   a resistive gas detector element connected between the common terminals of said first and second bridge circuit;
   at least three separate impedances which are not common to both bridge circuits contained in each of said first and second bridge circuits, wherein one of said separate impedances in said first bridge circuit is a resistive compensating element which is located in series with said resistive gas detector;
   means for deriving a signal indicative of gas concentration from across the output terminals of said first bridge circuit;
   a source of potential for powering said bridge circuits;
   a control element for varying the flow of current from said source of potential to said bridge circuits;
   and means coupled to the output terminals of said second bridge circuit for controlling said control element to maintain the effective resistance of said resistive gas detector element essentially constant.

2. The detector circuit of claim 1 wherein said first and second bridge circuits each have two legs connected between said input terminals, each leg containing two impedance elements in series with the junctions between the impedance elements in each leg comprising said output terminals.

3. The detector circuit of claim 2 wherein said controlling means and said source of potential are in series with said resistive detector element, said resistive compensating element and an impedance element in said second bridge circuit.

4. The detector circuit of claim 1 wherein said source of potential is connected to one input terminal of said second bridge circuit and is connected through said control element to one input terminal of said first bridge circuit.

5. The detector circuit of claim 4 wherein said control element comprises a transistor.

6. The detector circuit of claim 5 wherein said source of potential is connected to one input terminal of said first bridge circuit through the emitter and collector of said transistor.

7. The detector circuit of claim 6 wherein the means coupled to the output terminals of said second bridge circuit includes an operational amplifier, the output of said operational amplifier being connected to the base of said transistor.

* * * * *